(12) United States Patent
Hirasawa et al.

(10) Patent No.: US 8,853,460 B2
(45) Date of Patent: Oct. 7, 2014

(54) METHOD FOR SEPARATING CAROTENOID

(75) Inventors: Kazuaki Hirasawa, Tokyo (JP); Akira Tsubokura, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 249 days.

(21) Appl. No.: 13/146,724

(22) PCT Filed: Jan. 28, 2010

(86) PCT No.: PCT/JP2010/051130
§ 371 (c)(1),
(2), (4) Date: Oct. 14, 2011

(87) PCT Pub. No.: WO2010/087400
PCT Pub. Date: Aug. 5, 2010

(65) Prior Publication Data
US 2012/0059192 A1   Mar. 8, 2012

(30) Foreign Application Priority Data

Jan. 30, 2009   (JP) ................................. 2009-019935

(51) Int. Cl.
| | |
|---|---|
| C12N 9/00 | (2006.01) |
| C12N 1/20 | (2006.01) |
| C07C 45/00 | (2006.01) |
| C07C 35/21 | (2006.01) |
| C07C 11/00 | (2006.01) |
| C07C 13/00 | (2006.01) |

(52) U.S. Cl.
USPC ........ 568/324; 435/183; 435/252.3; 568/816; 585/16; 585/23

(58) Field of Classification Search
None
See application file for complete search history.

(56) References Cited

U.S. PATENT DOCUMENTS

| | | | |
|---|---|---|---|
| 5,607,839 A | 3/1997 | Tsubokura et al. | |
| 5,935,808 A | 8/1999 | Hirschberg et al. | |
| 5,962,756 A | 10/1999 | Koch et al. | |
| 7,745,170 B2 | 6/2010 | Tsubokura et al. | |
| 8,097,761 B2 | 1/2012 | Ishizaki et al. | |
| 2006/0121556 A1 | 6/2006 | Hirasawa et al. | |
| 2007/0054351 A1 | 3/2007 | Zhang | |
| 2007/0105189 A1 | 5/2007 | Tsubokura et al. | |
| 2009/0221026 A1 | 9/2009 | Tanaka et al. | |
| 2009/0298146 A1 | 12/2009 | Choi et al. | |
| 2010/0285524 A1 | 11/2010 | Tanaka et al. | |

FOREIGN PATENT DOCUMENTS

| | | | |
|---|---|---|---|
| CN | 1875112 A | | 12/2006 |
| EP | 0635576 A1 | | 1/1995 |
| EP | 1229126 A1 | | 8/2002 |
| EP | 1229126 A1 | * | 8/2002 |
| EP | 1496115 A1 | | 1/2005 |
| EP | 2 157 169 A1 | | 2/2010 |
| EP | 2345736 A1 | | 7/2011 |
| JP | 54-24940 A | | 2/1979 |
| JP | 05-276989 A | | 10/1993 |
| JP | 7-79796 A | | 3/1995 |
| JP | 11-69969 A | | 3/1999 |
| JP | 11-513707 A | | 11/1999 |
| JP | 2001-512030 A | | 8/2001 |
| JP | 2005-046027 A | | 2/2005 |
| JP | 2005-087099 A | | 4/2005 |
| JP | 2005-087100 A | | 4/2005 |
| JP | 2006-191919 A | | 7/2006 |
| JP | 2006-340676 A | | 12/2006 |
| JP | 2007-97584 A | | 4/2007 |
| JP | 2007-143492 A | | 6/2007 |
| JP | 2007-244205 A | | 9/2007 |
| JP | 2008-167665 A | | 7/2008 |
| JP | 2008-259452 A | | 10/2008 |
| NZ | 563130 A | | 4/2010 |
| WO | 88/08025 A1 | | 10/1988 |
| WO | 94/23057 A1 | | 10/1994 |
| WO | 97/15554 A1 | | 5/1997 |
| WO | WO9715554 A1 | * | 5/1997 |
| WO | 0196591 A1 | | 12/2001 |
| WO | 2005/118812 A1 | | 12/2005 |

OTHER PUBLICATIONS

Accession AAT15842. Aug. 15, 1996.*
An Extended European Search Report, mailed Dec. 10, 2012, which issued during the prosecution of European Patent Application No. 10735865.7, which corresponds to the present application.
A. Tsubokura, et al., *Paracoccus carotinifaciens* sp. nov., a new aerobic Gram-negative astaxanthin-producing bacterium, International Journal of Systematic Bacteriology, vol. 49, pp. 277-282, 1999.
E. Widmer, Synthetic advances in the carotenoid field, Pure & Appl. Chem., vol. 57, No. 5, pp. 741-752, 1985.
E. Widmer, et al., Technische Verfahren zur Synthese von Carotinoiden und verwandten Verbindungen aus 6-Oxo-isophoron. II. Ein neues Konzept fur die Synthese von (3RS,3'RS)-Astaxanthin1)2), Helvetica Chimica Acta, vol. 64, pp. 2436-2446, 1981.
J. H. Lee, et al., *Paracoccus haeundaensis* sp. nov., a Gram-negative, halophilic, astaxanthin-producing bacterium, International Journal of Systematic and Evolutionary Microbiology, vol. 54, pp. 1699-1702, 2004.
A. Berry, et al., *Paracoccus zeaxanthinifaciens* sp. nov., a zeaxanthin-producing bacterium, International Journal of Systematic and Evolutionary Microbiology, vol. 53, pp. 231-238, 2003.

(Continued)

*Primary Examiner* — Christian Fronda
(74) *Attorney, Agent, or Firm* — McDermott Will & Emery LLP (57) ABSTRACT

The present invention provides a method for collecting a carotenoid from a culture of a carotenoid-producing bacterium at high yield. Specifically, the present invention provides a method for separating a carotenoid comprising a step of precipitating a concentrate containing the carotenoid from a culture of a carotenoid-producing bacterium under acidic conditions; and a method for producing a carotenoid comprising the steps of precipitating a concentrate containing the carotenoid from a culture of a carotenoid-producing bacterium under acidic conditions and collecting the carotenoid from the obtained precipitate.

9 Claims, 1 Drawing Sheet

(56) References Cited

OTHER PUBLICATIONS

An Office Action, mailed Oct. 29, 2013, which issued in the prosecution of Japanese Application No. 2010-533939 which corresponds to U.S. Appl. No. 13/124,304, which is related to the present application.
A Supplementary European Search Report mailed Dec. 19, 2012, which issued during the prosecution of European Application No. 09 82 0647.7, which corresponds to U.S. Appl. No. 13/124,304, which is related to the present application.
Mel'Nikov, S.S. et al., "The effect of organic compounds on *Spirulina platensis* productivity and the carotenoid content" 1997, Database Biosis Biosciences Information Service, XP002688222.
An Office Action, mailed Dec. 3, 2012, which issued during the prosecution of Chinese Application No. 200980140867.4, which corresponds to U.S. Appl. No. 13/124,304, which is related to the present application.
Alper et al., Characterization of lycopene-overproducing *E.coli* strains in high cell density fermentations. Appl Microbiol Biotechnol., 2006, vol. 72: 968-974.
S. Alcantara, et al., Influence of carbon and nitrogen sources on *Flavobacterium* growth and zeaxanthin biosynthesis, Journal of Industrial Microbiology & Biotechnology, vol. 23, No. 1, pp. 697-700, 1999.

An Examination Report, issued on May 30, 2011, in New Zealand Application No. 592213, which corresponds to U.S. Appl. No. 13/124,304, which is related to the present application.
An Office Action, mailed Jul. 3, 2013, which issued during the prosecution of U.S. Appl. No. 13/124,304, which is related to the present application.
An Office Action, mailed Feb. 6, 2013, which issued during the prosecution of U.S. Appl. No. 13/124,304, which is related to the present application.
Office Action mailed Apr. 22, 2014, which issued during the prosecution of U.S. Appl. No. 13/124,304, which is related to the present application.
Kim et al., *Paracoccus homiensis* sp. nov., isolated from a sea-sand sample. Int. J. System. Evol. Biol., 2006, vol. 56: 2387-2390.
Pukall et al., *Paracoccus seriniphilus* sp. nov., an L-serine-dehydratase-producing coccus isolated from the marine bryozoan Bugula plumosa. Int. J. System. Evol. Biol., 2003, vol. 53: 443-447.
Office Action mailed Jul. 8, 2014, which issued during the prosecution of Japanese Patent Application No. 2010-533939, which is related to the present application.
K. S. Lusby et al., Condensed Molasses Solubles and Corn Steep Liquor as Protein Spplements for Range Cows, Oklahoma Agricultural Experiment Station, 1982, pp. 40-46.

\* cited by examiner

SEQUENCE LISTING

```
<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: Description of Unknown Organism: Paracoccus
```

```
                    carotinifaciens E-396
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga        60
gaccttcggg tctagcggcg gacgggtgag taacgcgtgg gaacgtgccc ttctctacgg       120
aatagccccg ggaaactggg agtaataccg tatacgccct ttgggggaaa gatttatcgg       180
agaaggatcg gcccgcgttg gattaggtag ttggtggggt aatggcccac caagccgacg       240
atccatagct ggtttgagag gatgatcagc cacactggga ctgagacacg gcccagactc       300
ctacgggagg cagcagtggg gaatcttaga caatggggc aaccctgatc tagccatgcc        360
gcgtgagtga tgaaggcctt agggttgtaa agctctttca gctgggaaga taatgacggt       420
accagcagaa gaagccccgg ctaactccgt gccagcagcc gcggtaatac ggaggggct        480 agcgttgttc ggaattactg ggcgtaaagc gcacgtaggc ggactggaaa gtcagaggtg       540
aaatcccagg gctcaaccct ggaactgcct ttgaaactat cagtctggag ttcgagagag       600
gtgagtggaa ttccgagtgt agaggtgaaa ttcgtagata tcggaggaa caccagtggc       660 gaaggcggct cactggctcg atactgacgc tgaggtgcga aagcgtgggg agcaaacagg       720
attagatacc ctggtagtcc acgccgtaaa cgatgaatgc cagacgtcgg caagcatgct       780
tgtcggtgtc acacctaacg gattaagcat tccgcctggg gagtacggtc gcaagattaa       840
aactcaaagg aattgacggg ggcccgcaca agcggtggag catgtggttt aattcgaagc       900
aacgcgcaga accttaccaa cccttgacat ggcaggaccg ctggagagat tcagctttct       960
cgtaagagac ctgcacacag gtgctgcatg gctgtcgtca gctcgtgtcg tgagatgttc      1020
ggttaagtcc ggcaacgagc gcaacccacg tccctagttg ccagcaattc agttgggaac      1080
tctatggaaa ctgccgatga taagtcgag gaaggtgtgg atgacgtcaa gtcctcatgg       1140
gccttacggg ttgggctaca cacgtgctac aatggtggtg acagtgggtt aatccccaaa      1200
agccatctca gttcggattg tcctctgcaa ctcgagggca tgaagttgga atcgctagta      1260
atcgcggaac agcatgccgc ggtgaatacg ttcccgggcc ttgtacacac cgcccgtcac      1320
accatgggag ttggttctac ccgacgacgn tgcgctaacc ttcgggggc aggcggccac       1380 ggtaggatca gcgactgggg tgaagtcgta acaaggtagc cgtaggggaa cctgcggctg      1440
gatcacctcc tt                                                          1452
```

METHOD FOR SEPARATING CAROTENOID

CROSS REFERENCE TO PRIOR APPLICATIONS

This application is a U.S. National Phase application under 35 U.S.C. §371 of International Application No. PCT/JP2010/051130, filed on Jan. 28, 2010 and claims benefit of priority to Japanese Patent Application No. 2009-019935, filed on Jan. 30, 2009. The International Application was published in Japanese on Aug. 5, 2010 as WO 2010/087400 A1 under PCT Article 21(2). All of these applications are herein incorporated by reference.

FIELD OF THE INVENTION

The present invention relates to a method for microbiologically producing a carotenoid. More particularly, the present invention relates to a method for separating a carotenoid that is usable as a feed additive, a food additive, a cosmetic ingredient, a pharmaceutical material or the like, such as astaxanthin, canthaxanthin, zeaxanthin, β-cryptaxanthin, lycopene, β-carotene, phoenicoxanthin, adonixanthin, echinenone, asteroidenone and 3-hydroxyechinenone, from a culture of a carotenoid-producing bacterium.

BACKGROUND OF THE INVENTION

Carotenoids are natural pigments that are useful as feed additives, food additives, cosmetic ingredients, pharmaceutical agents and the like. Examples of carotenoids include astaxanthin, canthaxanthin, zeaxanthin, β-cryptaxanthin, lycopene, β-carotene, phoenicoxanthin, adonixanthin, echinenone, asteroidenone and 3-hydroxyechinenone. Among them, astaxanthin is useful as feed additives, for example, as body color-improving agents for cultivated fishes such as salmon, trout and sea bream or as egg yolk color-improving agents for poultry. Moreover astaxanthin is highly valuable in the industries as safe natural food additives, healthy food materials, and cosmetic ingredients. Similar to astaxanthin, adonixanthin and phoenicoxanthin are also expected of their use as feed additives, food additives, cosmetic ingredients, pharmaceutical agents and the like once their industrial production methods are established. Furthermore, β-carotene is used as feed additives, food additives, cosmetic ingredients, pharmaceutical agents and the like; canthaxanthin is used as feed additives, food additives, cosmetics and the like; and zeaxanthin is used as food additives, feed additives, cosmetic ingredients and the like. In addition, lycopene, echinenone, β-cryptaxanthin, 3-hydroxyechinenone and asteroidenone are also expected of their use as feed additives, food materials, cosmetic ingredients and the like. Methods for producing these carotenoids include chemical synthesis processes, extraction from natural sources, production methods using microorganisms and the like.

As methods for chemically synthesizing astaxanthin, a method utilizing conversion of β-carotene (Non-patent Document 1: Pure Appl. Chem, 57, 741, 1985) and a method employing synthesis from C15 phosphonium salt (Non-patent Document 2: Helv. Chim. Acta, 64, 2436, 1981) are known. In addition, since astaxathin is present in fishes such as sea bream and salmon as well as crustaceans such as shrimp, crab and krill, it may also be extracted therefrom. Chemically synthesized astaxanthin is commercially available as a feed additive.

Methods that have been reported for producing astaxanthin using microorganisms include cultivation with green alga *Haemaococcus pluvialis* (Patent Document 1: Japanese Laid-Open Patent Publication No. 2007-97584), a fermentation process using red yeast *Phaffia rhodozyma* (Patent Document 2: Japanese Laid-Open Patent Publication No. H 11-69969), a fermentation process using a bacterium belonging to genus *Sphingomonas* (Patent Document 3: Japanese Laid-Open Patent Publication No. 2006-191919), a fermentation process using a bacterium belonging to genus *Brevundimonas* (Patent Document 4: Japanese Laid-Open Patent Publication No. 2006-340676), a fermentation process using a bacterium belonging to genus *Erythrobacter* (Patent Document 5: Japanese Laid-Open Patent Publication No. 2008-259452), and a fermentation process using a bacterium belonging to genus *Paracoccus* (hereinafter, also referred to as a "*Paracoccus* bacterium"). Examples of bacteria belonging to astaxanthin-producing genus *Paracoccus* include strains E-396 and A-581-1 (Patent Document 6: Japanese Laid-Open Patent Publication No. H 7-79796 and Non-patent Document 3: International Journal of Systematic Bacteriology (1999), 49, 277-282). Examples of other bacteria belonging to astaxanthin-producing genus *Paracoccus* include *Paracoccus marcusii* strain MH1 (Patent Document 7: Publication of Japanese translation of PCT international application No. 2001-512030), *Paracoccus haeundaensis* strain BC74171 (Non-patent Document 4: International Journal of Systematic and Evolutionary Microbiology (2004), 54, 1699-1702), *Paracoccus* bacterial strain N-81106 (Patent Document 8: Japanese Laid-Open Patent Publication No, 2007-244205), *Paracoccus zeaxanthinifaciens* (Non-patent Document 5: International Journal of Systematic and Evolutionary Microbiology (2003), 53, 231-238) and *Paracoccus* sp. strain PC-1 (Patent Document 9: WO 2005/118812).

There have been, however, several problems concerning the above-mentioned carotenoid production methods. For example, chemical synthetic methods have unfavorable impression on consumers from a safety perspective. Extraction from natural sources is associated with high production costs. In addition, production using a green alga or yeast is low in productivity and has difficulty in extraction of a carotenoid therefrom due to strong cell walls thereof.

Meanwhile, bacteria belonging to genus *Paracoccus* are advantageous in that their proliferation rates are rapid, their carotenoid productivity is high, and carotenoids can readily be extracted therefrom, etc. However, *Paracoccus* bacteria partially secrete carotenoids as vesicles outside the cells, and thus many carotenoids are dispersed as microparticles in the liquid. Therefore, it is difficult to remove supernatant from the culture and collect carotenoids at high yield. Conventional well-known carotenoid-producing bacteria beside *Paracoccus* bacteria, namely green algae *Haematococcus pluvialis* and red yeast *Phaffia rhodozyma*, have no such problem since carotenoids are entirely accumulated in the cells. In a culture of a carotenoid-producing *Paracoccus* bacterium, extracellular carotenoids may amount to as much as 80% of the entire carotenoids including the intracellular carotenoids. A method has been proposed for separating carotenoids from a culture of *Paracoccus* bacterium, which includes: centrifuging the culture at a first rate that is sufficient to pelletize the cells; collecting the supernatant containing carotenoids; and centrifuging the supernatant at a second rate that is sufficient to pelletize the carotenoid vesicles (Patent Document 4: Publication of Japanese translation of PCT international application No. 2001-512030). However, since carotenoids are present as very small particles in the culture supernatant, pelletization requires ultrafast centrifugation at a level of 100,000×g, which is impractical considering the costs of equipment and power.

RELATED ART DOCUMENTS

Patent Documents

Patent Document 1; Japanese Laid-Open Patent Publication No. 2007-97584
Patent Document 2: Japanese Laid-Open Patent Publication No. H 11-69969
Patent Document 3: Japanese Laid-Open Patent Publication No. 2006-191919
Patent Document 4; Japanese Laid-Open Patent Publication No. 2006-340676
Patent Document 5: Japanese Laid-Open Patent Publication No. 2008-259452
Patent Document 6: Japanese Laid-Open Patent Publication No, H 7-79796
Patent Document 7: Publication of Japanese translation of PCT international application No. 2001-512030
Patent Document 8: Japanese Laid-Open Patent Publication No. 2007-244205
Patent Document 9: International Patent Publication WO2005/118812

Non-Patent Documents

Non-patent Document 1: Pure Appl. Chem., 57, 741, 1985
Non-patent Document 2; Helv. Chim. Acta, 64, 2436, 1981
Non-patent Document 3: International Journal of Systematic Bacteriology (1999), 49, 277-282
Non-patent Document 4: International Journal of Systematic and Evolutionary Microbiology (2004), 54, 1699-1702.
Non-patent Document 5: International Journal of Systematic and Evolutionary Microbiology (2003), 53, 231-238

SUMMARY OF THE INVENTION

Problems to be Solved by the Invention

The present invention was made considering such situation with the purpose of providing a method which includes removing supernatant from a culture of a carotenoid-producing bacterium and collecting carotenoids therefrom at high yield.

Means For Solving the Problems

As a result of various studies for the purpose of solving the above-described problems, the present inventors found that a carotenoid can be separated at high yield by adjusting pH of a culture of a carotenoid-producing bacterium to acidic side prior to centrifugation, separation by filtration or decantation, thereby accomplishing the present invention.

Thus, the present invention relates to the following:
(1) A method for separating a carotenoid comprising a step of precipitating a concentrate containing the carotenoid and a bacterial body from a culture of a carotenoid-producing bacterium under acidic conditions.
(2) A method for producing a carotenoid comprising the steps of: precipitating a concentrate containing the carotenoid and a bacterial body from a culture of a carotenoid-producing bacterium under acidic conditions; and collecting the carotenoid from the obtained precipitate.
(3) The method according to (1) or (2) above, wherein the acidic conditions are pH5.5 or less.
(4) The method according to (1) or (2) above, wherein the acidic conditions are adjusted by adding an acid to the culture.
(5) The method according to (4) above, wherein the acid is at least one selected from the group consisting of sulfuric acid, hydrochloric acid, nitric acid, acetic acid, citric acid, succinic acid, phosphoric acid, malic acid, butyric acid, propionic acid, oxalic acid, gluconic acid, tartaric acid, phthalic acid, carbonic acid and ascorbic acid.
(6) The method according to (1) or (2) above, wherein the carotenoid is at least one selected from the group consisting of astaxanthin, canthaxanthin, zeaxanthin, β-cryptoxanthin, lycopene, β-carotene, phoenicoxanthin, adonixanthin, echinenone, asteroidenone and 3-hydroxyechinenone.
(7) The method according to (1) or (2) above, wherein the bacterium is a bacterium belonging to genus *Paracoccus*.
(8) The method according to (1) or (2) above, wherein a base sequence of DNA that corresponds to 16S ribosomal RNA of the bacterium has a homology of 95% or higher with the base sequence represented by SEQ ID NO:1.
(9) The method according to (1) or (2) above, wherein the bacterium is strain E-396 (FERM BP-4283), strain A-581-1 (FERM BP-4671) or a mutant thereof.
(10) The method according to (1) above, wherein the step of precipitating the concentrate is carried out by at least one selected from the group consisting of centrifugation, separation by filtration and decantation.
(11) A carotenoid-containing composition obtained by the method according to any one of (1) to (10) above.

Effect of the Invention

According to the present invention, a carotenoid can be collected at high yield by removing supernatant from a culture.

EMBODIMENTS FOR CARRYING OUT THE INVENTION

Hereinafter, the present invention will be described in more detail. The scope of the present invention should not be limited by these descriptions and may appropriately be carried out apart from the following illustrative embodiments without departing from the spirit of the present invention.

All of the publications cited herein, for example, related art documents, Japanese laid-open patent applications, Japanese patent publications and other patent documents, are incorporated herein by reference in their entirety. The present specification incorporates the content of the specification of Japanese Patent Application No. 2009-019935 (filing date: Jan. 30, 2009) based on which the present application claims priority.

The present invention relates to a method for culturing a carotenoid-producing bacterium and producing a carotenoid therefrom, the method comprising the steps of precipitating a carotenoid-containing concentrate from the culture by centrifugation, separation by filtration or decantation under acidic conditions. According to the method of the present invention, a carotenoid can be produced at a low cost.

Although a bacterium used for the present invention is not limited at all as long as it is a carotenoid-producing bacterium, it is preferably a bacterium belonging to genus *Para-*

*coccus, Sphingomonas, Brevundimonas* or *Etythrobacter*, and particularly preferably a bacterium belonging to genus *Paracoccus*. Among the bacteria belonging to genus *Paracoccus, Paracoccus carotinifaciens, Paracoccus marcusii, Paracoccus haeundaensis* and *Paracoccus zeaxanthinifaciens* are preferably used, and *Paracoccus carotinifaciens* is particularly preferably used. Specific examples of bacterial strains belonging to genus *Paracoccus* include *Paracoccus carotinifaciens* strain E-396 (FERM BP-4283) and *Paracoccus* bacterial strain A-581-1 (FERM BP-4671), where their mutants can also preferably be used for the present invention.

Moreover, as a carotenoid-producing bacterium, a bacterium whose base sequence of DNA corresponding to 16S ribosomal RNA is highly homologous with the base sequence of strain E-396 represented by SEQ ID NO:1 can preferably be used. The phrase "having high homology" as used herein means that the base sequence represented by SEQ ID NO:1 and a corresponding base sequence of a bacterium of interest are homologous for preferably 95% or higher, more preferably 96% or higher, still more preferably 97% or higher, particularly preferably 98% or higher, and most preferably 99% or higher.

A base sequence of DNA corresponding to 16S ribosomal RNA refers to a base sequence obtained by substituting U (uracil) in the base sequence of 16S ribosomal RNA with T (thymine).

This classification of microorganisms based on the homology of the base sequence of 16S ribosomal RNA is recently becoming the mainstream. Since conventional classifications of microorganisms are based on mycological properties of the microorganisms such as mobility, auxotrophy, sugar utilization and the like, the microorganisms may incorrectly be classified when there is a change in the characteristics or the like due to spontaneous mutation. On the other hand, since the base sequence of 16S ribosomal RNA is fairly genetically stable, classification based on its homology greatly improves reliability of the classification as compared to the conventional classifications.

Homologies between the base sequence of 16S ribosomal RNA of *Paracoccus carotinifaciens* strain E-396 and the base sequences of 16S ribosomal RNAs of other carotenoid-producing bacteria, i.e., *Paracoccus marcusii* strain DSM 11574, *Paracoccus* bacterial strain N-81106, *Paracoccus haeundaensis* strain BC 74171, *Paracoccus* bacterial strain A-581-1, *Paracoccus zeaxanthinifaciens* strain ATCC 21588 and *Paracoccus* sp. strain PC-1 are 99.7%, 99.7%, 99.6%, 99.4%, 95.7% and 95.4%, respectively, showing that these strains are extremely close strains in terms of taxonomy. Therefore, these strains may be regarded as making one group of carotenoid-producing bacteria. Accordingly, these strains may preferably be used for the present invention for efficient production of carotenoids.

According to the present invention, mutant strains having improved carotenoid productivity can also be used. Examples of improved mutant strains include strains with high astaxanthin-producing capacity (Japanese Laid-Open Patent Application No, 2001-95500), strains that selectively and mainly produce canthaxanthin (Japanese Laid-Open Patent Application No. 2003-304875), strains that selectively and mainly produce zeaxanthin and β-cryptoxanthin (Japanese Laid-Open Patent Application No, 2005-87097), strains that selectively produce lycopene (Japanese Laid-Open Patent Application No. 2005-87100) and strains with improved sedimentation property.

Mutant strains with improved carotenoid productivity can be acquired by mutation treatment and screening. The method for mutation treatment is not particularly limited as long as it induces mutation. For example, chemical methods using a mutagen such as N-methyl-N'-nitro-N-nitrosoguanidine (NTG) or ethyl methanesulfonate (EMS); physical methods such as ultraviolet irradiation and X-ray irradiation; and biological methods such as genetic recombination and transposon can be used. Microorganisms to be subjected to the mutation treatment are not particularly limited, but they are preferably carotenoid-producing bacteria. Furthermore, mutant strains may be those obtained by naturally-occurring mutation.

The method for screening a mutant strain is not particularly limited, and may be, for example, a method in which a mutant strain of interest is selected according to the color tone of a colony on an agar medium, or a method in which mutant strains are cultured in a test tube, a flask, a fermenter or the like and the mutant strain of interest is selected according to a carotenoid pigment analysis utilizing absorbance, high-performance liquid chromatography, thin-layer chromatography or the like.

The steps of mutation and screening may be performed once or may be repeated twice or more such that, for example, mutant strains are obtained by a mutation treatment and screening, and subjected to another mutation treatment and screening to obtain a mutant strain with improved productivity.

Examples of carotenoids produced according to the present invention include, but not particularly limited to, astaxanthin, canthaxanthin, zeaxanthin, β-cryptoxanthin, lycopene, β-carotene, phoenicoxanthin, adonixanthin, echinenone, asteroidenone or 3-hydroxyechinenone, and preferably xanthophylls (i.e., oxygen-containing carotenoids) such as astaxanthin, canthaxanthin, zeaxanthin β-cryptoxanthin, phoenicoxanthin, adonixanthin, echinenone, asteroidenone or 3-hydroxyechinenone. More preferably, the carotenoid is astaxanthin, canthaxanthin, phoenicoxanthin, adonixanthin, zeaxanthin or β-cryptoxanthin, and still more preferably astaxanthin. One type of carotenoid or a combination of multiple types of carotenoids may be produced according to the present invention. A carotenoid having a hydroxyl group such as astaxanthin, zeaxanthin, β-cryptoxanthin, phoenicoxanthin, adonixanthin or the like may exist in an ester form with fatty acid, in a glucoside form bound to sugar or in a free form unbound to any compound. Although a carotenoid obtained according to a method of the present invention may exist in any of the above-mentioned forms, it particularly preferably exists in a free form.

Hereinafter, a method for culturing the above-described bacteria according to the present invention will be described.

A medium used for the cultivation for producing a carotenoid according to the present invention may be any medium as long as it allows the growth of the carotenoid-producing bacterium and the production of the carotenoid. Preferably, a medium containing a carbon source, a nitrogen source, or an inorganic salt and if necessary a vitamin is used.

Examples of carbon sources inch sugars such as glucose, sucrose, lactose, fructose, trehalose, mannose, mannitol and maltose; organic acids such as acetic acid, fumaric acid, citric acid, propionic acid, malic acid, malonic acid and pyruvic acid; alcohols such as ethanol, propanol, butanol, pentanol, exanol, isobutanol and glycerol; and lipids such as soybean oil, bran oil, olive oil, corn oil, sesame oil and linseed oil, among which glucose or sucrose is preferably used. One or more types of these carbon sources can be used. The amount added to a preculture medium (starting medium) differs depending on the type of the carbon source and may appropriately be adjusted, but it is usually 1-100 g, and preferably 2-50 g per 1 L of the medium. The carbon source can be added not only to the starting medium but it may also preferably be additionally supplied during cultivation in a sequential continuous manner.

One or more types of inorganic nitrogen sources can be used among ammonium salts such as ammonium nitrate, ammonium sulfate, ammonium chloride and ammonium phosphate, nitrate salts such as potassium nitrate, ammonia and urea. The amount added differs depending on the type of the nitrogen source and may appropriately be adjusted, but it is usually 0.1 g-20 g, and preferably 0.2-10 g per 1 L of the medium.

One or more organic nitrogen sources can be used, for example, among corn steep liquor (including filtrated products), pharmamedia, soybean meal, soybean flour, peanut meal, Distillers' solubles, dried yeast and monosodium glutamate. The concentration for addition differs depending on the type of the nitrogen source and may appropriately be adjusted, but it is usually 0-80 g/L, and preferably 0-30 g/L medium.

The inorganic nitrogen source and the organic nitrogen source are usually added to the starting medium, but they may also preferably be additionally supplied during cultivation in a sequential or continuous manner.

One or more inorganic salts can be used, for example, among phosphoric salts such as potassium dihydrogen phosphate, dipotassium hydrogen phosphate and disodium hydrogen phosphate; magnesium salts such as magnesium sulfate and magnesium chloride; iron salts such as ferric sulfate and ferric chloride; calcium salts such as calcium chloride and calcium carbonate; sodium salts such as sodium carbonate and sodium chloride; manganese salts such as manganese sulfate; cobalt salts such as cobalt chloride; copper salts such as copper sulfate; zinc salts such as zinc sulfate; molybdenum salts such as sodium molybdate; nickel salts such as nickel sulfate; selenium salts such as sodium selenate; boric acid and potassium iodide. The amount added differs depending on the type of the inorganic salt and may appropriately be adjusted, but it is usually 0.0001-15 g per 1 L of the medium. The inorganic salt is usually added to the starting medium, but they may also be additionally supplied in a sequential or continuous manner.

Examples of vitamins which can be used include cyanocobalamin, riboflavin, pantothenic acid, pyridoxine, thiamine, ascorbic acid, folic acid, niacin, p-aminobenzoic acid, biotin, inositol and choline. The proportion for addition differs depending on the type of the vitamin and may appropriately be adjusted, but it is usually 0.001-1000 mg, and preferably 0.01-100 mg per 1 L of the medium. The vitamin is usually added to the starting medium, but they may also be additionally supplied in a sequential or continuous manner.

According to the present invention, an antifoamer is preferably used in order to prevent formation of bubbles in the culture. Any type of antifoamer ea be used as long as it can prevent generation of bubbles and disappear the generated bubbles with less inhibition effect on the produced bacterium. Examples include alcohol-based antifoamers, polyether-based antifoamers, ester-based antifoamers, fatty acid-based antifoamers, silicon-based antifoamers and sulfonic acid-based antifoamers. The amount added differs depending on the type of the antifoamer and may appropriately be adjusted, but it is usually 0.01 g-10 g per 1 L if the medium.

The antifoamer is usually added to the starting medium prior to sterilization. It may also be additionally supplied during cultivation in a continuous or intermittent manner.

A medium for producing a carotenoid used in the present invention is sterilized before being used for culturing a bacterium. Sterilization can appropriately be carried out by those skilled in the art. For example, the medium in a suitable reservoir can be subjected to heating in an autoclave. Alternatively, filtration sterilization may be carried out using a sterilizing filter.

The initial pH of the medium used for producing a carotenoid in the present invention is adjusted to 2-12, preferably 6-9, and more preferably 6.5-8.0. Preferably, pH within this range is maintained during cultivation. Examples of pH regulators include an aqueous sodium hydroxide solution, an aqueous potassium hydroxide solution, an aqueous sodium carbonate solution, ammonia water, ammonia gas, an aqueous sulfuric acid solution and a mixture thereof.

According to the present invention, a carotenoid-producing bacterium is inoculated to the medium for producing a carotenoid prepared as described, above and cultured under predetermined conditions. Inoculation is carried out by appropriately growing the strain by seed cultivation using a test tube, a flask, a fermenter or the like, and adding the resulting culture to the medium for producing a carotenoid. The medium used for seed cultivation is not particularly limited as long as it provides good growth of the carotenoid-producing bacterium.

Cultivation is carried out in a suitable cultivation reservoir. The cultivation reservoir can appropriately be selected according to the of cultivation, including, for example, a test tube, a flask, a fermenter or the like.

The temperature for cultivation is 15-80° C., preferably 20-35° C. and more preferably 25° C.-32° C. for usually 1-20 days, preferably 2-12 days and more preferably 3-9 days under aerobic conditions. Examples of aerobic conditions include shaking cultivation and aeration/agitation cultivation, where the concentration of the dissolved oxygen is preferably controlled to fall within a certain range. The concentration of the dissolved, oxygen may be controlled, for example, by changing the number of rotation for agitation, the amount of aeration, internal pressure or the like. The concentration of the dissolved oxygen is controlled to be preferably 0.3-10 ppm, more preferably 0.5-7 ppm and still more preferably 1-5 ppm.

The present invention is characterized, by carrying out the step of precipitating a concentrate containing a carotenoid and the bacterial bodies from the culture obtained by cultivating a carotenoid-producing bacterium as described above by centrifugation, separation by filtration or decantation (i.e., the step of separating a carotenoid) under acidic conditions. Since acidic conditions allow carotenoids dispersed in the culture supernatant to aggregate and increase the particle sizes thereof and improve the sedimentation property, the culture can readily be separated into a supernatant and a concentrate containing the carotenoids and the bacterial bodies upon the separation step. The term "culture" as used herein refers to any one of culture supernatant, cultured bacterial bodies or fragments of the bacterial cells.

A method for preparing acidic conditions for cultivation is usually carried out by adding an acid to the culture. According to another method, pH adjustment with alkali is terminated at the late phase of the cultivation since pH decreases as the carbon source is consumed during the cultivation of the present invention, and cultivation is terminated once pH reaches to an acidic point appropriate for separation.

Any acid can be used for providing acidic conditions for the culture, including, for example, sulfuric acid, hydrochloric acid, nitric acid, acetic acid, citric acid, succinic acid, phosphoric acid, malic acid, butyric acid, propionic acid, oxalic acid, gluconic acid, tartaric acid, phthalic acid, carbonic acid and ascorbic acid. The acid may be a solution at a highest concentration or may be diluted with water or the like.

Any pH can be employed for acidic conditions as long as it is within an acidic range, while its upper limit should preferably be pH 5.5 or lower, more preferably pH 5.2 or lower and still more preferably pH 4.9 or lower. There is no limit to the lower limit, but it is preferably pH 0.5 or higher, and more preferably pH 1.5 or higher, pH adjustment is generally carried out by adding an acid while monitoring pH of the culture with a pH electrode.

The culture can be subjected to the separation process directly after adjusting its pH to be in an acidic range. The culture can also preferably be diluted with water before separation in order to enhance the effect of removing unnecessary components. In this case, the pH adjustment of the culture may be conducted before or after the addition of water. Water can also be added during the process of centrifugation, separation by filtration, decantation or the like. There is no limit to the amount of water added for dilution while it is preferably 0-10 times, more preferably 0.5-3.0 times the volume of the culture. Furthermore, heat sterilization can also be conducted following the cultivation to kill the cultured microorganism before separation. In this case, pH may be adjusted before or after the heat sterilization.

While the method for separating a carotenoid according to the present invention can be any method that allows separation based on the sedimentation property or based on the size of the particles, centrifugation, separation by filtration or decantation is preferably employed. These may be employed alone or two or more of them may be employed in combination. Alternatively, the same type of separation may be repeated twice or more such that, for example, centrifugation is performed once and then again for the supernatant only to collect the carotenoids remaining in the supernatant.

The centrifuge used for centrifugation may be either a continuous centrifuge or a batch centrifuge, while a continuous centrifuge is preferably used. Any type of centrifuge may be used, including, for example, a basket-type, multichamber-type, decanter-type, disk-type (nozzle-type, desludge-type), tubular-type and rotor-type centrifuges. Any level of centrifugal acceleration employed for separation of common bacterial bodies can be employed while it is preferably 500-100,000×g, and more preferably 1,000-50,000×g.

A membrane filtration apparatus used for separation by filtration may be either a static type or a crossflow type, while a crossflow type that is more likely to prevent clogging is favorable. Examples of the material used for the membrane include filter paper, filter cloth, chemical fiber and ceramic. In addition, a filter aid such as diatomaceous earth may also be used. Examples of a system for promoting filtration include a pressure-type, reduced pressure-type, centrifugal filtration-type and filter press-type systems while examples of the type of the membrane include a flat membrane, a hollow fiber membrane and a cylindrical membrane. Any pore size of the membrane may be used as long as it is suitable for generally separating the bacteria while it is preferably 0.001-100 μm, more preferably 0.01-10 μm and still more preferably 0.1-1 μm. A microfiltration membrane or an ultrafiltration membrane is preferably used, and a microfiltration membrane is particularly preferably used.

Any reservoir can be used for decantation. For example, a general cylindrical tank may be used. The time for leaving the culture to stand for decantation is not particularly limited, but it is preferably 0.5 h-48 h and more preferably 1 h-24 h.

The temperature of the culture subjected to separation is not particularly limited as long as it is at a general temperature, but it is preferably 0° C.-90° C., more preferably 2° C.-75° C. and still more preferably 4° C.-60° C.

Carotenoids and bacterial bodies can be concentrated in the precipitated concentrate obtained from the culture by the above-described separation step, namely, centrifugation, separation by filtration, decantation a combination thereof. Preferably, the separation speed, separation strength and the like can appropriately be controlled such that the viscosity and the moisture content of the precipitated concentrate stay appropriate for the next step. The recovery rate of the carotenoids in the concentrate following the separation step may vary depending on the effects such as degradation and deterioration of the carotenoids, adhesion of the carotenoids to the inner surface or the like of the apparatus and leakage of the carotenoids to the supernatant, but it is preferably 70-100%, more preferably 80-100%, and still more preferably 90-100%.

Dry bacterial bodies containing carotenoids can be obtained by drying the resulting precipitated concentrate. The thus-obtained dry bacterial bodies can directly be used as a feed additive. Alternatively, carotenoids can be extracted from the dry bacterial bodies and purified as necessary to be used for foods, cosmetics or feeds. Carotenoids can be extracted and collected from the precipitated concentrate without drying to produce carotenoids. The method of drying is not particularly limited, and includes, for example, spray drying, fluidized drying, spray drying granulation, fluidized spray drying granulation, rotary drum drying and lyophilization. In addition, one or more treatments among a chemical treatment using, thr example, an alkali reagent or a surfactant, a biochemical treatment using, for example, a lytic enzyme, a lipid degrading enzyme or a protein degrading enzyme, or a physical treatment such as ultrasound, pulverization or heating can be performed at the stage of a culture, a precipitated concentrate or dry bacterial bodies.

Examples of a solvent used for extraction and washing upon extraction of carotenoids from the culture include, but not limited to, lower alcohols such as methanol, ethanol and isopropanol, acetone, tetrahydrofuran, methyl ethyl ketone, methyl isobutyl ketone, dichloromethane, chloroform, dimethylformamide, dimethylsulfoxide and hexane.

The thus-obtained extract may directly be used as a carotenoid or may further be purified before use. The method for separating bacterial bodies or the like from the extract following the extraction process is not particularly limited, while filtration, centrifugation, decantation or the like may be used. A method for obtaining a carotenoid precipitate from the extracted liquid may be, for example, a precipitation method by cooling, heating, vacuum condensation, addition of a poor solvent, addition of any salt such as acid/alkali agents or a combination thereof. If necessary, the resulting carotenoid precipitate may be subjected to suspension/agitation for washing using a solvent such as a small amount of lower alcohol. Means for washing is not particularly limited, while practically preferable methods include a method in which filtration is performed following suspension/agitation and a method in which a liquid is passed from above the precipitate.

In order to prevent degradation of carotenoids caused by oxidation as much as possible in the culture, the precipitated concentrate, the dry bacterial bodies, the extracted liquid, the purified product and in each process, the processes may be carried out under an inert gas atmosphere such as nitrogen gas. Moreover, an antioxidant used for pharmaceutical agents and foods may be selected for addition. Alternatively, these treatments may be employed in combination. In addition, in order to prevent degradation of carotenoids caused by light as much as possible, the processes may be carried out under lightless conditions.

The thus-obtained precipitated concentrate, dry bacterial bodies, extract or purified product may be used alone as a carotenoid or they may be mixed and used with each other at any proportions.

Hereinafter, the present invention will be described specifically by way of examples, although the scope of the present invention should not be limited to the following examples.

Carotenoids in the examples were quantified as follows using high-performance liquid chromatography (HPLC).

Two Wakosil-II 5 SIL-100 columns (φ4.6×250 mm) (Wako Pure Chemical Industries, Ltd.) were used in tandem. Elution can be performed by running an n-hexane-tetrahydrofuran-methanol mixture solution (40:20:1) as a mobile phase at 1.0 mL/minute at a constant temperature around room temperature. For measurement, samples dissolved with tetrahydrofuran were 100-fold diluted with the mobile phase and 20 μL of the resultant was injected. The column eluent was detected at a wavelength of 470 nm. Furthermore, astaxanthin (produced by Sigma) (Cat. No. A9335) was used as a standard preparation for quantification. The concentration of astaxanthin in the standard solution was determined according to the following formula after measuring (A) the absorbance of the standard solution at 477 nm and (B) the area percentage % of astaxanthin peak upon HPLC analysis under the above-described conditions.

$$\text{Concentration of astaxanthin (mg/L)} = A/2150 \times B \times 100$$

Example 1

A hundred ml of a medium having the following composition (sucrose 30 g/L, corn steep liquor 30 g/L, potassium dihydrogen phosphate 0.54 g/L, dipotassium hydrogen phosphate 2.78 g/L, calcium chloride dihydrate 0.1 g/L, magnesium sulfate heptahydrate 12 g/L, ferric sulfate heptahydrate 0.3 g/L, pH7.2) was poured into a 500 ml conical flask and sterilized in an autoclave at 121° C. for 15 minutes to prepare a flask medium for seeding.

Then, 2.0 L of a medium having the following composition (sucrose 20 g/L, corn steep liquor 30 g/L, potassium dihydrogen phosphate 1.5 g/L, disodium hydrogen phosphate dodecahydrate 3.8 g/L, calcium chloride dihydrate 0.2 g/L, magnesium sulfate heptahydrate 3.0 g/L, ferric sulfate heptahydrate 1.0 g/L, alcoholic antifoamer 0.5 g/L) was poured into a 5 L, fermenter and sterilized in an autoclave at 121° C. for 30 minutes.

A loopful of *Paracoccus carotinifaciens* strain E-396 (FERM BP-4283) was inoculated into the flask medium for seeding and subjected to rotary shaking cultivation at 150 rpm at 28° C. for 2 days. Subsequently, 80 mL of the resulting culture was inoculated into the fermenter for aerobic cultivation at 28° C. with an aeration volume of lvvm for 100 hours. pH during cultivation was continuously controlled with 20% NaOH to stay at 7.2. Addition of 30 g of glucose took place on the first and second days so as to prevent depletion of the carbon source. In addition, the number of agitation rotation was varied such that the concentration of the dissolved oxygen in the culture maintained 2-4 ppm with the minimum number of agitation rotation being 200 rpm. Once bubble formation was detected with a bubble sensor, an alcohol-based antifoamer was automatically added to inhibit bubble formation. The concentrations of the carotenoids in the culture at the end of the cultivation were measured. The results are shown in Table 1. Moreover, pH of the culture was measured to be pH6.7.

TABLE 1

| | Concentrations of carotenoids (mg/L) |
|---|---|
| β-carotene | 3.95 |
| Echinenone | 1.62 |
| 3-Hydroxyechinenone | 0.33 |
| Canthaxanthin | 1.90 |
| Phoenicoxanthin | 4.95 |
| β-cryptoxanthin | 0.04 |
| Astaxanthin | 19.86 |
| Asteroidenone | 0.40 |
| Adonixanthin | 6.05 |
| Zeaxanthin | 0.21 |
| Total carotenoid | 39.31 |

Thirty ml of the resulting culture was collected into each of eight beakers while stirring, where one was left to be pH 6.7 and the rest seven being adjusted to be pH 5.5, pH 5.2, pH 4.9, pH 4.1, pH 3.0, pH1.5 and pH0.5, respectively with a 25% aqueous sulfuric acid solution. Each of the cultures was placed into a 50 ml centrifuge tube and subjected to centrifugation using an angle rotor at a centrifugal acceleration of 3,000×g at 50° C. for 10 minutes. Following the centrifugation, the centrifuge tube was immediately tilted upside down above a different reservoir to remove the supernatant for separation from the precipitated concentrate as pellets attached to the bottom of the centrifuge tube. Without further purification, carotenoids in the precipitated concentrate were analyzed and the separation recovery rate of each carotenoid component was calculated according to the following formula:

Recovery rate %=weight of each carotenoid component in precipitated concentrate (mg)/weight of each carotenoid component in culture prior to separation (mg)×100

Figure 1:
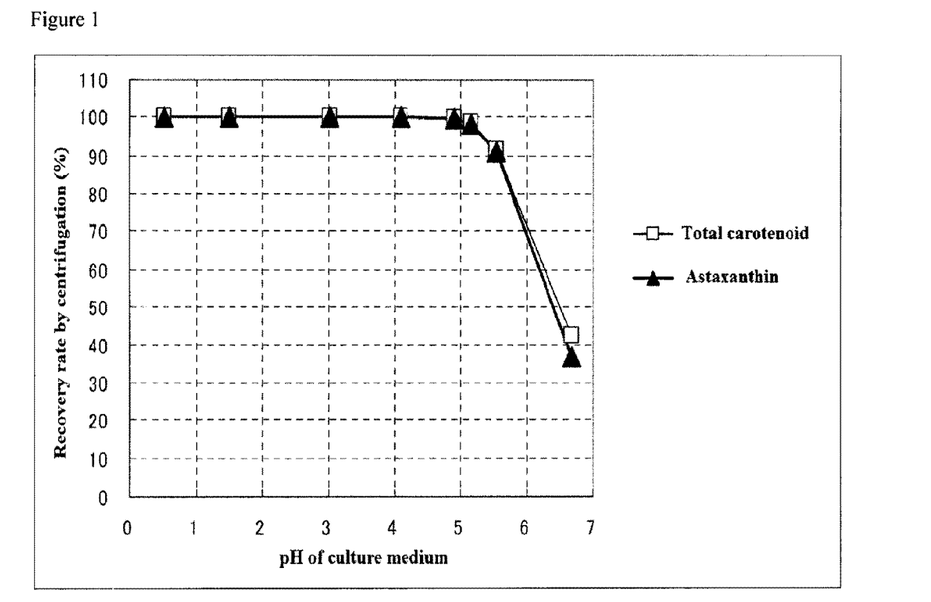
FIG. 1 is a diagram showing recovery rates of carotenoids separated by centrifugation at various pH.

The separation recovery rates of carotenoids from cultures at various pH are shown in Table 2 and FIG. 1. The recovery rates of astaxanthin and total carotenoid were 50% or less at pH 6.7 while they were 90% or higher at pH 5.5 or lower.

TABLE 2

| Carotenoid recovery rates % after centrifugation | | | | | | | | |
|---|---|---|---|---|---|---|---|---|
| | Culture pH | | | | | | | |
| | 6.7 | 5.5 | 5.2 | 4.9 | 4.1 | 3.0 | 1.5 | 0.5 |
| β-carotene | 71 | 94 | 99 | 100 | 100 | 100 | 100 | 100 |
| Echinenone | 69 | 93 | 99 | 100 | 100 | 100 | 100 | 100 |
| 3-Hydroxyechinenone | 64 | 93 | 99 | 100 | 100 | 100 | 100 | 100 |
| Canthaxanthin | 54 | 93 | 99 | 100 | 100 | 100 | 100 | 100 |
| Phoenicoxanthin | 40 | 92 | 99 | 100 | 100 | 100 | 100 | 100 |
| β-cryptoxanthin | 70 | 91 | 96 | 100 | 100 | 100 | 100 | 100 |
| Astaxanthin | 37 | 91 | 98 | 100 | 100 | 100 | 100 | 100 |
| Asteroidenone | 44 | 87 | 98 | 100 | 100 | 100 | 100 | 100 |
| Adonixanthin | 51 | 90 | 97 | 100 | 100 | 100 | 100 | 100 |
| Zeaxanthin | 72 | 92 | 96 | 100 | 100 | 100 | 100 | 100 |
| Total carotenoid | 43 | 91 | 98 | 100 | 100 | 100 | 100 | 100 |

Figure 2:
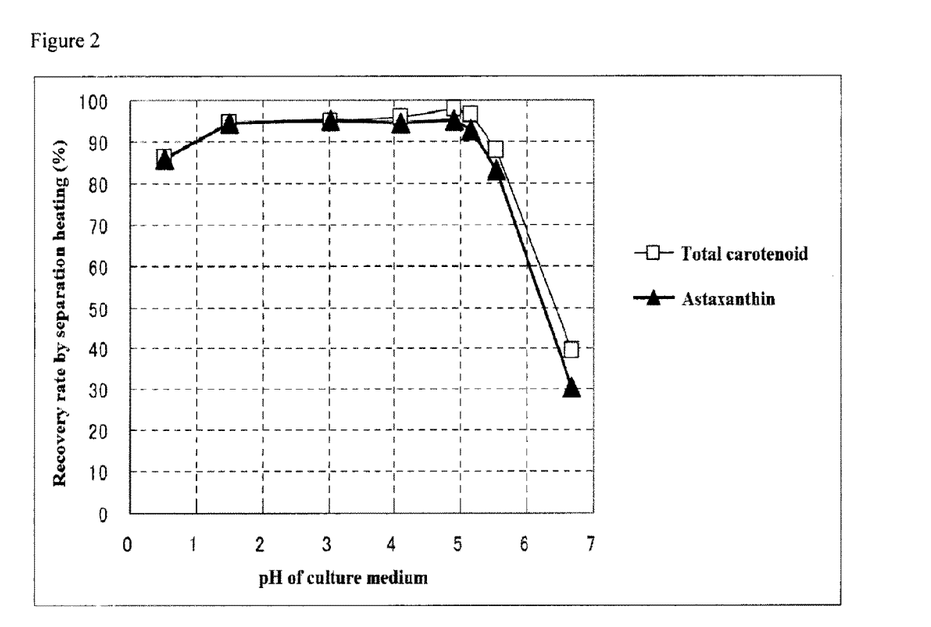
FIG. 2 is a diagram showing recovery rates of carotenoids separated by centrifugation and then subjected to heating treatment at various pH.

Next, in order to study the stability of carotenoids in the precipitated concentrate during the heat sterilization step, drying step, preserving step and the like following the separation step, the resulting precipitated concentrate was subjected to heating treatment in an autoclave at 121° C. for an hour. The concentrations of carotenoids in the precipitated concentrate after the heating treatment were analyzed to obtain the recovery rates for the culture prior to the centrifugation, which are shown in Table 3 and FIG. 2. Following the separation step, the recovery rate of the total carotenoid contained in the precipitated concentrate subjected to heating treatment was 80% or higher at pH 0.5-5.5.

TABLE 3

Carotenoid recovery rates % after centrifugation/heating treatment

| | Culture pH | | | | | | | |
|---|---|---|---|---|---|---|---|---|
| | 6.7 | 5.5 | 5.2 | 4.9 | 4.1 | 3.0 | 1.5 | 0.5 |
| β-carotene | 58 | 81 | 87 | 87 | 82 | 79 | 78 | 73 |
| Echinenone | 70 | 92 | 97 | 98 | 96 | 93 | 93 | 84 |
| 3-Hydroxyechinenone | 59 | 84 | 91 | 93 | 91 | 88 | 92 | 83 |
| Canthaxanthin | 55 | 93 | 97 | 99 | 98 | 97 | 98 | 91 |
| Phoenicoxanthin | 39 | 92 | 99 | 99 | 97 | 95 | 94 | 86 |
| β-cryptoxanthin | 37 | 75 | 85 | 84 | 83 | 80 | 84 | 62 |
| Astaxanthin | 31 | 83 | 93 | 95 | 95 | 95 | 94 | 86 |
| Asteroidenone | 43 | 86 | 96 | 96 | 97 | 93 | 95 | 75 |
| Adonixanthin | 39 | 76 | 84 | 86 | 85 | 83 | 84 | 75 |
| Zeaxanthin | 33 | 47 | 50 | 51 | 50 | 49 | 48 | 42 |
| Total carotenoid | 39 | 88 | 96 | 98 | 96 | 95 | 95 | 86 |

Example 2

*Paracoccus carotinifaciens* strain E-396 was subjected to mutation treatment with N-methyl-N'-nitro-N-nitrosoguanidine, and a colony presenting strong red color tone was selected. Carotenoids in the culture of the selected strain were analyzed and Y-1071 mutant strain with enhanced astaxanthin productivity was selected.

Six ml of a medium having the following composition (sucrose 30 g/L, corn steep liquor 30 g/L, potassium dihydrogen phosphate 0.54 g/L, dipotassium hydrogen phosphate 2.78 g/L, calcium chloride dihydrate 0.1 g/L, magnesium sulfate heptahydrate 12 g/L, ferric sulfate heptahydrate 0.3 g/L, pH7.2) was poured into a 18 mm-diameter test tube and sterilized in an autoclave at 121° C. for 15 minutes to prepare a test tube medium for seeding.

Then, 100 mL of a medium having the following composition (glucose 40 g/L, corn steep liquor 30 g/L, potassium dihydrogen phosphate 1.5 g/L, &odium hydrogen phosphate dodecahydrate 3.8 g/L, calcium chloride dihydrate 0.2 g/L, magnesium sulfate heptahydrate 3.0 g/L, ferric sulfate heptahydrate 1.0 g/L, pH7.2) was poured into a 500 mL Sakaguchi flask and sterilized in an autoclave at 121° C. for 15 minutes.

A loopful of *Paracoccus* bacterial strain Y-1071 was inoculated into the test tube medium for seeding and subjected to cultivation with reciprocating shaking at 300 spm at 28° C. for 2 days. Then, 2 mL of the culture was inoculated into the flask medium and subjected to cultivation with reciprocating shaking at 120 spm at 28° C. for 3 days. The concentrations of carotenoids in the culture at the end of the cultivation were measured. The results are shown in Table 4. The pH of the culture was measured to be pH 6.7.

TABLE 4

| | Concentrations of carotenoids (mg/L) |
|---|---|
| β-carotene | 6.8 |
| Echinenone | 3.7 |
| 3-Hydroxyechinenone | 0.5 |
| Canthaxanthin | 5.7 |
| Phoenicoxanthin | 13.9 |
| β-cryptoxanthin | 0.1 |
| Astaxanthin | 48.4 |
| Asteroidenone | 0.9 |

TABLE 4-continued

| | Concentrations of carotenoids (mg/L) |
|---|---|
| Adonixanthiy | 11.6 |
| Zeaxanthin | 0.3 |
| Total carotenoid | 91.9 |

Thirty ml of the resulting culture was collected into two beakers while stirring, where one was left to be pH6.7 and the other being adjusted to pH5.2 with a 25% aqueous sulfuric acid solution. Each of the cultures was placed into a 50 ml centrifuge tube and subjected to centrifugation using an angle rotor at a centrifugal acceleration of 3,000×g at 50° C. for 10 minutes. Following the centrifugation, the centrifuge tube was immediately tilted upside down above a different reservoir to remove the supernatant for separation from the precipitated concentrate as pellets attached to the bottom of the centrifuge tube. Carotenoids in the precipitated concentrate were analyzed and the separation recovery rates were calculated according to the formula described in Example 1. The separation recovery rates of the carotenoids in the cultures with different pH are shown in Table 5. The recovery rates of astaxanthin and total carotenoid at pH5.2 were 100%, showing that separation was significantly enhanced by lowering pH in mutant strain Y-1071.

TABLE 5

Carotenoid recovery rates % by centrifugation

| | pH 6.7 | pH 5.2 |
|---|---|---|
| β-carotene | 78 | 100 |
| Echinenone | 66 | 100 |
| 3-Hydroxyechinenone | 65 | 100 |
| Canthaxanthin | 58 | 100 |
| Phoenicoxanthin | 45 | 100 |
| β-crytoxanthin | 76 | 100 |
| Astaxanthin | 46 | 100 |
| Asteroidenone | 49 | 100 |
| Adonixanthin | 65 | 99 |
| Zeaxanthin | 50 | 99 |
| Total carotenoid | 52 | 100 |

Thirty ml of the resulting culture was adjusted to pH 4.8 with a 20% aqueous acetic acid solution. The resultant was subjected to suction filtration with a Kiriyama-rohto funnel using 60 mm-diameter No. 5C filter paper for 10 minutes for separation into a precipitated concentrate and a filtrate. Carotenoids in the resulting concentrated precipitate were measured and the recovery rates by filtration were determined according to the formula described in Example 1. Thirty ml of the culture at pH 6.7 was similarly subjected to separation by filtration and both results are shown in Table 6. For separation by filtration, yields were improved by lowering pH.

TABLE 6

Carotenoid recovery rates % by separation by filtration

| | pH 6.7 | pH 4.8 |
|---|---|---|
| β-carotene | 24 | 94 |
| Echinenone | 24 | 95 |
| 3-Hydroxyechinenone | 30 | 98 |
| Canthaxanthin | 24 | 95 |
| Phoenicoxanthin | 24 | 94 |
| β-cryptoxanthin | 24 | 94 |
| Astaxanthin | 27 | 97 |
| Asteroidenone | 23 | 96 |

TABLE 6-continued

Carotenoid recovery rates % by separation by filtration

|  | pH 6.7 | pH 4.8 |
| --- | --- | --- |
| Adonixanthin | 24 | 96 |
| Zeaxanthin | 24 | 95 |
| Total carotenoid | 26 | 96 |

Example 3

Six ml of a medium having the following composition (sucrose 30 g/L, corn steep liquor 30 g/L, potassium dihydrogen phosphate 0.54 g/L, dipotassium hydrogen phosphate 2.78 g/L, calcium chloride dihydrate 0.1 g/L, magnesium sulfate heptahydrate 12 g/L, ferric sulfate heptahydrate 0.3 g/L, pH 7.2) was poured into a 18 mm-diameter test tube and sterilized in an autoclave at 121° C. for 15 minutes to prepare a test tube medium for seeding.

Subsequently, 100 mL of a medium having the following composition (glucose 40 g/L, corn steep liquor 30 g/L, potassium dihydrogen phosphate 1.5 disodium hydrogen phosphate dodecahydrate 3.8 g/L, calcium chloride dihydrate 0.2 g/L, magnesium sulfate heptahydrate 3.0 g/L, ferric sulfate heptahydrate 1.0 g/L, pH 7.2) was poured into a 500 mL Sakaguchi flask and sterilized in an autoclave at 121° C. for 15 minutes.

A loopful of *Paracoccus* bacterial strain A-581-1 (FERM BP-4671) was inoculated into the test tube medium for seeding and subjected to cultivation with reciprocating shaking at 300 spm at 28° C. for 2 days. Then, 2 mL of the culture was inoculated into the flask medium and subjected to cultivation with reciprocating shaking at 120 spin at 28° C. for 3 days. The concentrations of carotenoids in the culture at the end of the cultivation were measured as shown in Table 7. pH of the culture was 6.6.

TABLE 7

|  | Concentrations of carotenoids (mg/L) |
| --- | --- |
| β-carotene | 0.71 |
| Echinenone | 0.22 |
| 3-Hydroxyechinenone | 0.03 |
| Canthaxanthin | 0.30 |
| Phoenicoxanthin | 0.74 |
| Astaxanthin | 2.72 |
| Asteroidenone | 0.03 |
| Adonixanthin | 1.36 |
| Zeaxanthin | 0.02 |
| Total carotenoid | 6.13 |

Thirty ml of the resulting culture was adjusted to pH 4.9 with a 20% aqueous hydrochloric acid solution. Thirty ml of this culture and the original pH 6.6 culture were each placed into a 50 ml centrifuge tube and subjected to centrifugation using a swing rotor at a centrifugal acceleration of 2,000×g for 10 minutes. Following the centrifugation, the centrifuge tube was immediately tilted upside down above a different reservoir to remove the supernatant for separation from the precipitated concentrate as pellets attached to the bottom of the centrifuge tube. The carotenoids in the precipitated concentrates were analyzed and the separation recovery rates of carotenoids were calculated according to the formula described in Example 1. The separation recovery rates of the carotenoids are shown in Table 8. The recovery rate was 100% at pH 4.9.

TABLE 8

Carotenoid recovery rates % by centrifugation

|  | pH 6.6 | pH 4.9 |
| --- | --- | --- |
| β-carotene | 68 | 100 |
| Echinenone | 63 | 100 |
| 3-Hydroxyechinenone | 60 | 100 |
| Canthaxanthin | 52 | 100 |
| Phoenicoxanthin | 38 | 100 |
| Astaxanthin | 35 | 100 |
| Asteroidenone | 42 | 100 |
| Adonixanthin | 50 | 100 |
| Zeaxanthin | 68 | 100 |
| Total carotenoid | 45 | 100 |

INDUSTRIAL APPLICABILITY

As described above, a carotenoid can be collected at high yield by a microbiological method for producing a carotenoid according to the present invention.

[Accession Numbers]

Strain E-396 exemplified as a carotenoid-producing bacterium used in the present invention has been deposited as international deposition to the International Patent Organism Depositary, the National Institute of Advanced Industrial Science and Technology as follows:

International Deposition Authority: International Patent Organism Depositary, National Institute of Advanced Industrial Science and Technology (former National Institute of Bioscience and Human-Technology. Agency of Industrial Science and Technology, Ministry of International Trade and Industry) Central 6, Higashi 1-1-1, Tsukuba-shi, 305-8566

Identification Indication: E-396

Accession No: FERM BP-4283

Date of original deposition: Apr. 27, 1993 (Heisei 5)

In addition, strain A-581-1 exemplified as other carotenoid-producing bacterium used in the present invention has been deposited as international deposition to the above-mentioned authority as follows:

Identification Indication: A-581-1

Accession No: FERM BP-4671

Date of original deposition: May 20, 1994 (Heisei 6)

The invention claimed is:

1. A method for producing a carotenoid comprising the steps of:
    precipitating a concentrate containing the carotenoid and a bacterial body from a culture of a carotenoid-producing bacterium under acidic conditions; and
    collecting the carotenoid from the obtained precipitate, wherein the carotenoid is at least one selected from the group consisting of astaxanthin, canthaxanthin, zeaxanthin, β-cryptoxanthin, phoenicoxanthin, adonixanthin, echinenone, asteroidenone and 3-hydroxyechinenone.

2. The method according to claim 1, wherein the acidic conditions are pH5.5 or less.

3. The method according to claim 1, wherein the acidic conditions are adjusted by adding an acid to the culture.

4. The method according to claim 3, wherein the acid is at least one selected from the group consisting of sulfuric acid, hydrochloric acid, nitric acid, acetic acid, citric acid, succinic acid, phosphoric acid, malic acid, butyric acid, propionic acid, oxalic acid, gluconic acid, tartaric acid, phthalic acid, carbonic acid and ascorbic acid.

5. The method according to claim 1, wherein the bacterium is a bacterium belong to genus *Paracoccus*.

6. The method according to claim 1, wherein the carotenoid-producing bacterium is a bacterium whose nucleotide sequence of DNA corresponding to 16S ribosomal RNA has a homology of 95% or higher with the nucleotide sequence represented by SEQ ID NO:1.

7. The method according to claim 1, wherein the bacterium is strain E-396 (FERM BP-4283), strain A-581-1 (FERM BP-4671) or a mutant strain thereof.

8. The method according to claim 1, wherein the step of precipitating the concentrate is carried out by at least one selected from the group consisting of centrifugation, separation by filtration and decantation.

9. A carotenoid-containing composition obtained by the method according to claim 1.

* * * * *